United States Patent [19]

Ife et al.

[11] Patent Number: 4,820,708

[45] Date of Patent: Apr. 11, 1989

[54] PYRIMIDYLALKYLTHIO BENZIMIDAZOLE COMPOUNDS, PHARMACEUTICAL COMPOSITIONS AND USE

[75] Inventors: Robert J. Ife, Stevenage; Thomas H. Brown, Tewin, both of England

[73] Assignee: Smith Kline & French Laboratories, Welwyn Garden City, England

[21] Appl. No.: 223,181

[22] Filed: Jul. 22, 1988

Related U.S. Application Data

[62] Division of Ser. No. 829,366, Feb. 14, 1986, Pat. No. 4,777,172.

[30] Foreign Application Priority Data

Mar. 5, 1985 [GB] United Kingdom ................ 8505615
Dec. 23, 1985 [GB] United Kingdom ................ 8531605

[51] Int. Cl.$^4$ ................ A61K 31/505; A61K 31/535; C07D 491/056
[52] U.S. Cl. ................ 514/232.8; 514/253; 514/256; 514/819; 544/122; 544/295; 544/327
[58] Field of Search ................ 544/122, 295, 317; 514/232.8, 253, 256

[56] References Cited

FOREIGN PATENT DOCUMENTS 0178438 4/1986 European Pat. Off. .

Primary Examiner—Robert W. Ramsuer
Attorney, Agent, or Firm—Nancy S. Mayer; Stuart R. Suter; Alan D. Lourie

[57] ABSTRACT

This invention relates to 2- and 4-pyrimidinylmethylsulphinyl(and thio)benzimidazoles in which the pyrimidyl group is substituted by an optionally substituted amino group. These compounds inhibit exogenously and endogenously stimulated gastric acid secretion.

10 Claims, No Drawings

PYRIMIDYLALKYLTHIO BENZIMIDAZOLE COMPOUNDS, PHARMACEUTICAL COMPOSITIONS AND USE

This is a divisional of application Ser. No. 829,366 filed Feb. 14, 1986, now U.S. Pat. No. 4,777,172.

The present invention relates to novel substituted benzimidazole derivatives, intermediates useful in their preparation, pharmaceutical compositions containing them and a method of inhibiting gastric acid secretion by administering them.

Substituted benzimidazole derivatives that are capable of inhibiting gastric acid secretion are known in the art. For example, GB No. 1500043 and GB No. 1525958 disclose a series of 2-pyridylalkyltiio- and 2-pyridylalkylsulphinyl benzimidazoles in which the pyridyl group is optionally mono-substituted by an alkyl or a halogen group. Further, EP Nos. 5129B, 74341A and 80602A disclose series of 2-pyridylalkylsulphinyl- and 2-pyridylalkylthio-benzimidazoles in which the pyridyl group is optionally substituted by 1 to 3 substituents selected from methyl, ethyl, methoxy, ethoxy, methoxyethoxy or ethoxyethoxy; and GB No. 2134523A discloses further such compounds in which the pyridyl group is optionally substituted by 1 to 3 groups. Such compounds are believed to exert their effects by inhibition of the gastro-intestinal $H^+$-$K^+$ ATPase enzyme. (Fellenius E., Berglindh T., Sachs G., Olke L., Elander B., Sjostrand S. E. and Wallmark B., 1981, Nature, 290, 159–61).

In addition, U.S. Pat. No. 4,359,465 discloses the cytoprotective action of certain 2-pyridylalkylthio- and 2-pyridylalkylsulphinyl-benzimidazoles and their use in the treatment or prevention of gastro-intestinal inflammatory disease.

It has now been found that 2- or 4-pyrimidylalkylsulphinyl (and thio) benzimidazoles in which the pyrimidyl group is substituted by an optionally substituted amino group inhibit exogenously and endogenously stimulated gastric acid secretion.

The present invention therefore provides, in a first aspect, a compound of structure (I)

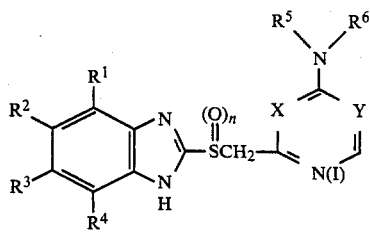

in which, $R^1$ to $R^4$ are the same or different and are each hydrogen, $C_{1-6}$alkyl, halogen, trifluoromethyl, $C_{1-6}$alkoxy, $C_{1-6}$alkanoyl, $C_{1-6}$alkoxycarbonyl, $RCF_2O$, an ethoxy group substituted by 3 to 5 fluorine atoms, or $R^2$ and $R^3$ together form a group $-O(CR_2)_mO-$ where m is 1 or 2, and each group R is hydrogen or fluorine;

n is 0 or 1;

$R^5$ and $R^6$ are the same or different and are each hydrogen, $C_{1-6}$alkyl or $C_{3-6}$cycloalkyl, or $R^5$ and $R^6$ together with the nitrogen atom to which they are attached form an azetidino, pyrrolidino, piperidino, piperazino, $N$-$C_{1-4}$alkylpiperazino or morpholino group; and one of X and Y is a nitrogen atom, and the other is a group $CR^7$ where $R^7$ is hydrogen, $C_{1-6}$alkyl or $NH_2$; or a pharmaceutically acceptable salt thereof.

Suitably, $R^1$ to $R^4$ are all hydrogen. More suitably, $R^1$ and $R^4$ are hydrogen, one of $R^2$ and $R^3$ is hydrogen and the other is halogen, trifluoromethyl, $RCF_2O$, an ethoxy group substituted by 3 to 5 fluorine atoms, $C_{1-6}$alkoxycarbonyl or $C_{1-6}$alkanoyl. Preferably, $R^1$ and $R^4$ are hydrogen, one of $R^2$ and $R^3$ is hydrogen, and the other is $C_{1-6}$alkyl or $C_{1-6}$alkoxy; or $R^1$ and $R^4$ are hydrogen and $R^2$ and $R^3$ are the same or different and are each $C_{1-6}$alkyl or $C_{1-6}$alkoxy or together form a group $-O(CR_2)_mO-$.

Suitably, ethoxy groups substituted by 3 to 5 fluorine atoms are, 2,2,2-trifluoroethoxy, 1,1,2-trifluoroethoxy, 1,2,2-trifluoroethoxy, 1,1,2,2-tetrafluoroethoxy, 1,2,2,2-tetrafluoroethoxy, and perfluoroethoxy.

Suitably, groups $-O(CR_2)_mO-$ in which m is 1 are for example, difluoromethylene dioxy ($-OCF_2O-$); preferably methylenedioxy ($-OCH_2O-$); suitably, groups $-O(CR_2)_mO-$ in which m is 2 are ethylenedioxy ($-OCH_2CH_2O-$) and trifluoroethylenedioxy ($-OCHFCF_2O-$).

Suitably n is 0. Preferably n is 1.

Suitably one of $R^5$ and $R^6$ is hydrogen and the other is $C_{3-6}$cycloalkyl. Preferably $R^5$ and $R^6$ are the same or different and are each hydrogen or $C_{1-6}$alkyl.

Suitably $R^5$ and $R^6$ together with the nitrogen atom to which they are attached form an azetidino group. Preferably, $R^5$ and $R^6$ together with the nitrogen atom to which they are attached form a morpholino, pyrrolidino, piperazino, $NC_{1-4}$alkylpiperazino or piperidino group.

Suitably $R^7$ is $NH_2$. Preferably $R^7$ is hydrogen or $C_{1-6}$alkyl.

$C_{1-6}$Alkyl groups alone or as part of another group (for example $C_{1-6}$alkoxy, $C_{1-6}$alkoxycarbonyl or $C_{1-6}$alkanoyl), can be straight or branched, for example methyl, ethyl, n-propyl, i-propyl, i-butyl, s-butyl, n-butyl, n-pentyl, i-pentyl or n-hexyl. Preferably $C_{1-6}$alkyl groups are methyl or ethyl.

Preferably, $C_{1-6}$ alkoxy groups are methoxy or ethoxy.

Preferably $C_{1-6}$alkoxycarbonyl groups are methoxycarbonyl or ethoxycarbonyl.

Preferably $C_{1-6}$alkanoyl groups are methanoyl or ethanoyl.

$C_{3-6}$Cycloalkyl groups are cyclopropyl, cyclobutyl, cyclopentyl and cyclohexyl. Preferably, $C_{3-6}$ cycloalkyl groups are cyclopentyl or cyclohexyl.

Examples of compounds of the present invention include, (i) compounds of structure (I) in which X is nitrogen, Y is $CR^7$ and n is 1, for example, 5-methoxy-2-(4-piperidino-2-pyrimidinylmethylsulphinyl)-(1H)-benzimidazole 5-methoxy-2-(4-morpholino-2-pyrimidinylmethylsulphinyl)-(1H)-benzimidazole 5-methoxy-2-(4-pyrrolidino-2-pyrimidinylmethylsulphinyl)-(1H)-benzimidazole 5-methoxy-2-(4-dimethylamino-2-pyrimidinylmethylsulphinyl)-(1H)-benzimidazole 5-methoxy-2-(4-piperidino-5-methyl-2-pyrimidinylmethylsulphinyl)-(1H)-benzimidazole 5-methoxy-2-(4-piperidino-5-amino-2-pyrimidinylmethylsulphinyl)-(1H)-benzimidazole 5-methoxy-2-(4-dimethylamino-5-methyl-2-pyrimidinylmethylsulphinyl)-(1H)-benzimidazole 5-methoxy-2-(4-dimethylamino-5-amino-2-pyrimidinylmethylsulphinyl)-(1H)-benzimidazole;

(ii) compounds of structure (I) in which X is CR⁷, Y is nitrogen and n is 1, for example, 5-methoxy-2-(5-methyl-6-piperidino-4-pyrimidinylmethylsulphinyl)-(1H)-benzimidazole 5-methoxy-2-(5-methyl-6-pyrrolidino-4-pyrimidinylmethylsulphinyl)-(1H)-benzimidazole 5-methoxy-2-(5-methyl-6-morpholino-4-pyrimidinylmethylsulphinyl)-(1H)-benzimidazole 5-methoxy-2-(5-methyl-6-dimethylamino-4-pyrimidinylmethylsulphinyl)-(1H)-benzimidazole 5-methoxy-2-(6-piperidino-4-pyrimidinylmethylsulphinyl)-(1H)-benzimidazole 5-methoxy-2-(6-pyrrolidino-4-pyrimidinylmethylsulphinyl)-(1H)-benzimidazole 5-methoxy-2-(6-dimethylamino-4-pyrimidinylmethylsulphinyl)-(1H)-benzimidazole; and (iii) the corresponding thioethers of the foregoing compounds, ie the analogous compounds in which n is 0.

Compounds of structure (I) in which n is 0, can form pharmaceutically acceptable acid addition salts with suitable organic and inorganic acids, the nature of which will be apparent to persons skilled in the art. For example, pharmaceutically acceptable salts can be formed by reaction with hydrochloric, sulphuric, sulphonic or phosphonic acids; aliphatic, alicyclic, aromatic or heterocyclic carboxyl or sulphonic acids; methionine, tryptophan, lysine or arginine and the like.

Compounds of structure (I) in which n is 1 can also form pharmaceutically acceptable acid addition salts, but in aqueous solution the salts are less stable than those formed with the compounds of structure (I) in which n is 0.

Compounds of structure (I) in which n is 1 can form basic salts by reaction with an appropriate base. Such salts include, for example the sodium, potassium, lithium, calcium and magnesium salts, which can be prepared by methods well known to those skilled in the art; for example, the sodium, potassium and lithium salts can be prepared by reaction with sodium, potassium or lithium hydroxide in an aqueous or non-aqueous medium, and the calcium salts can be prepared by reaction of the sodium, lithium or potassium salts with calcium chloride in an aqueous or non-aqueous medium.

Compounds of structure (I) in which n is 0 can also form basic salts but less readily than the compounds of structure (I) in which n is 1.

Compounds of structure (I) in which n is 1 have an asymmetric centre at the S atom and are thus optically active compounds. As such, these compounds exist as two optical isomers (enantiomers). In addition, compounds of structure (I) in which one or more of R¹ to R⁸ is a branched $C_{3-6}$ alkyl group (either alone or as part of another group) may contain an additional asymmetric centre(s) due to the presence of the $C_{3-6}$ alkyl group(s). Again, such compounds will exist as two (or more) optical isomers.

Both the pure enantiomers, racemic mixtures (50% of each enantiomer) and unequal mixtures ofthe two are included within the scope of the present invention. Further, all diasteriomeric forms possible (pure enantiomers and mixtures thereof) are within the scope of the invention.

It should be noted that for all the compounds of the present invention, the substituents R¹ and R⁴ as well as R² and R³ are considered to be equivalent at room temperature in solution. This is due to the tautomerism of the benzimidazole nucleus causing an equilibrium between the 2 possible forms.

Processes for the preparation of compounds of structure (I) and pharmaceutically acceptable salts thereof comprise (a) reacting a compound of structure (II)

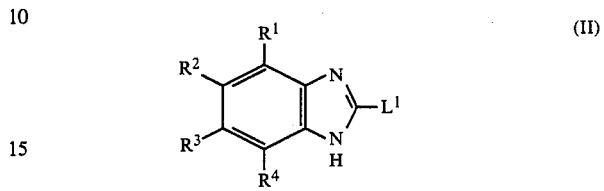

with a compound of structure (III)

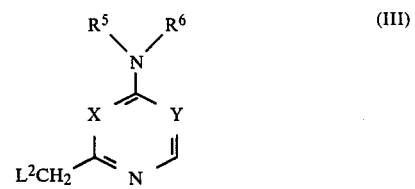

in which R¹ to R⁶, X and Y are as described for structure (I) and one of L¹ and L² is SH and the other is a leaving group displaceable by a mercaptan;

(b) reacting a compound of structure (IV)

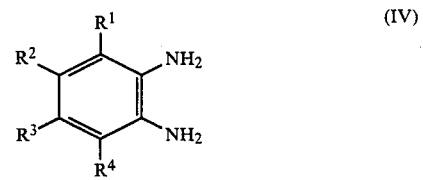

in which R¹ to R⁴ are as described for structure (I), with a compound of structure (V)

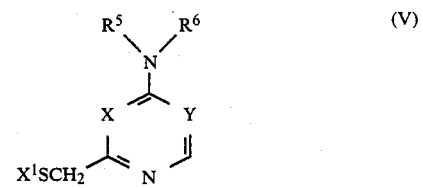

in which R⁵, R⁶, X and Y are as described for structure (I), X¹ is CO₂H or CSX² and X² is halogen or $C_{1-4}$alkoxy;

(c) reacting a compound of structure (VI)

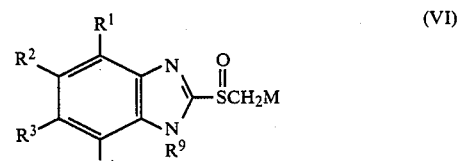

in which R¹ to R⁴ are as described for structure (I), R⁹ is hydrogen or a protecting group and M is an alkali metal atom, with a compound of structure (VII)

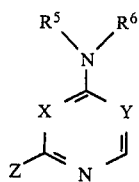

(VII)

in which $R^5$, $R^6$, X and Y are as described for structure (I) and Z is a leaving group;

(d) reacting a compound of structure (VIII)

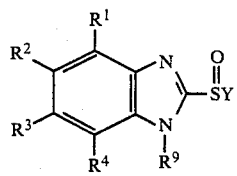

(VIII)

in which $R^1$ to $R^4$ are as described for structure (I), $R^9$ is hydrogen or a protecting group and Y is a leaving group, with a compound of structure (IX)

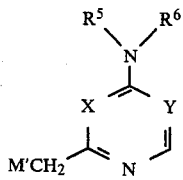

(IX)

in which $R^5$, $R^6$, X and Y are as described for structure (I) and M' is an alkali metal atom or the equivalent of an alkali metal atom, and, optionally, where desired:
(i) oxidising a compound of structure (I) so formed in which n is 0 to a compound of structure (I) in which n is 1;
(ii) reducing a compound of structure (I) so formed in which n is 1 to a compound of structure (I) in which n is 0;
(iii) removing any protecting group $R^9$;
(iv) forming a pharmaceutically acceptable salt.

Suitable leaving groups $L^1$ displaceable by mercaptan include halogen, for example chloro, bromo or iodo, arylsulphonyloxy for example toluenesulphonyloxy, alkylsulphonyloxy for example methanesulphonyloxy, alkylmercapto, for example methylmercapto, alkylsulphinyl, for example methylsulphinyl, or alkylsulphonyl for example methylsulphonyl.

Suitable leaving groups $L^2$ are as described for $L^1$, and may also be $C_{1-4}$acyloxy, for example acetoxy, or hydroxy.

Suitable alkali metal atoms M include, for example lithium, sodium or potassium.

Suitable leaving groups Z include, for example, halogen (preferably chloro) and hydroxy activated by esterification with, for example, an aryl or alkane sulphonic acid. Suitable sulphonic acids will be apparent to those skilled in the art, for example p-toluenesulphonic acid or methanesulphonic acid.

Suitable leaving groups Y are those groups which form a reactive sulphinic acid derivative together with the sulphinyl group to which it is attached, and include for example, $C_{1-4}$alkoxy, di-$C_{1-4}$alkylamino and $C_{1-4}$alkylmercapto.

Suitable groups M' which are equivalent to a metal atom include, for example, alkali earth metal atoms, (for example magnesium) which are substituted by a halogen atom (for example, bromine).

Suitable protecting groups $R^9$ are those conventional in the art for example as described in "Protective Groups in Organic Synthesis" T. W. Greene 1981 (Wiley). It will be appreciated that the group $R^9$ should not be cleavable under the conditions of reaction of compounds of structure (VIII) and (IX). Such groups include for example benzyl or trityl groups.

The reaction between compounds of structure (II) in which $L^1$ is SH and compounds of structure (III) in which $L^2$ is a leaving group can be carried out under basic conditions in the presence of an inert solvent at a temperature between ambient and the reflux temperature of the solvent.

Suitable solvents include lower alkanols, for example methanol or ethanol, mixtures of lower alkanols with water, or ethers, for example dimethoxyethane or tehrahydrofuran.

Suitable bases will be apparent to those skilled in the art and include for example, alkali metal hydroxides, for example, sodium or potassium hydroxide, alkali metal alkoxides, for example potassium t-butoxide, alkali metal hydrides, for example sodium or potassium hydride, or organic tertiary amines, for example triethylamine.

Preferably the reaction is carried out at ambient temperature in ethanol as solvent, in the presence of sodium hydroxide solution.

It is to be noted, and will be apparent to persons skilled in the art that under basic conditions $L^2$ should be a group other than hydroxy or acetoxy, for example halogen, preferably chlorine.

Further, the reaction can be carried out under neutral conditions in the presence of an inert solvent at the reflux temperature of the solvent. Suitable solvents include those hereinbefore described.

Alternatively, when $L^2$ is hydroxy or $C_{1-4}$acyloxy, for example acetoxy, the reaction can be carried out under acidic conditions. Suitable acidic conditions will be well known to those skilled in the art, for example, under reflux in hydrobromic acid, optionally in the presence of acetic acid.

The reaction between compounds of structure (II) in which $L^1$ is a leaving group and compounds of structure (III) in which $L^2$ is SH can be carried out under basic conditions as described for the reaction between compounds of structure (II) in which $L^1$ is SH and compounds of structure (III) in which $L^2$ is a leaving group.

The reaction between compounds of structure (IV) and compounds of structure (V) can be carried out under acidic conditions in a suitable solvent at a temperature between ambient and reflux temperature of the solvent used.

Suitably the reaction is carried out in polar solvents, for example, lower alkanols, dimethyl sulphoxide, acetone, dimethylformamide or acetonitrile, optionally in the presence of water. Preferably the reaction is carried out in ethanol.

Suitably the reaction is carried out in the presence of a strong acid, for example hydrobromic or hydrochloric acid. Preferably the reaction is carried out in the presence of hydrochloric acid.

Preferably the reaction is carried out at the reflux temperature of the solvent.

The reaction between a compound of structure (VI) and a compound of structure (VII) can be carried out in an inert solvent at ambient or elevated temperature depending on the nature of groups M and Z. Suitable solvents include those solvents usually employed for the reaction of enolate ions with alkylating agents, for example, tetrahydrofuran, diethylether, benzene or toluene. Preferably, when M is lithium and Z is chlorine, the reaction is conducted in benzene at reflux temperature.

The reaction between a compound of structure (VIII) and a compound of structure (IX) can be carried out in an organic solvent, for example, tetrahydrofuran or diethylether, under conditions normally used for organometallic reactions as will be well known to those skilled in the art.

The products of reactions (a) to (c) are compounds of structure (I) in which n is 0. These products can be oxidised to compounds of structure (I) in which n is 1 by reaction with an oxidising agent. Suitable oxidising agents include, for example, nitric acid, hydrogen peroxide, peracids, peresters, ozone, dinitrogen tetroxide, iodosobenzene, N-halosuccinamide, 1-chlorobenzotriazole, hypohalites, for example sodium hypochlorite or t-butyl hypochlorite, diazabicylo [2,2,2]-octane bromine complex, sodium metaperiodate, selenium dioxide, manganese dioxide, chromic acid, ceric ammonium nitrate, bromine, chlorine, or sulphuryl chloride. Preferably the oxidising agent is m-chloroperbenzoic acid.

The oxidation reaction is carried out under conditions known in the art for the oxidation of thiols to sulphoxides. Suitably, the reaction is carried out in an inert solvent at a temperature of between −70° and the boiling point of the solvent used. Suitable solvents include aromatic or chlorinated hydrocarbons, for example benzene, toluene, dichloromethane or chloroform, esters, for example ethyl acetate, or ethers, for example dioxan. Preferably, the reaction is carried out in dichloromethane at a temperature of between −50° and +20° C.

The compounds of structure (I) are obtained either as the free base, or in the form of a salt depending on the choice of starting materials and reaction conditions. If the free compound is obtained it can be converted into a salt by standard techniques well-known to those skilled in the art, for example by dissolving the compound in a suitable solvent and adding the desired acid or base; alternatively, if a salt is obtained it can be converted into the free compound, again by standard techniques, for example by treatment with an appropriate acid or base.

Racemic mixtures may be produced and can be separated by standard techniques e.g. recrystallisation from optically active solvent or by high performance liquid affinity chromatography as described by S. Allenmark, B. Bomgren, H. Baren and P-O Lagerstrom in Analytical Biochemistry, 136, 293–7, 1984.

The intermediates of structure (IV) and the intermediate benzimidazole structures (II), (VI) and (VIII) are known or can be prepared by methods analogous to those known in the art. For example compounds of structure (II) in which $L^1$ is SH can be prepared by reacting the corresponding compounds of structure (IV) with carbon disulphide in the presence if alkali metal hydroxides, or with potassium ethylxanthate (Org. Syn., 30, 56) or thiophosgene. Compounds of structure (II) in which $L^1$ is a leaving group, for example halogen can be obtained from the corresponding compounds of structure (II) in which $L^1$ is hydroxy by treatment with for example, phosphorous oxychloride. The compounds of structure (II) in which $L^1$ is hydroxy can be prepared by reacting compounds of structure (IV) with phosgene. Compounds of structure (IV) can be prepared by methods analogous to those described in EP No. 127763A, DE No. 2848531, CA, 60, 13352h, 1964 and Liebigs Ann. Chem., 730, 16–30, 1969.

Compounds of structure (VI) can be prepared by methylation, oxidation and protection (i.e. introduction of the group $R^9$) of compounds of structure (II) in which $L^1$ is SH.

Compounds of structures (III), (V), (VII) and (IX) are novel and provide a further aspect of the invention. They can be prepared by methods analogous to those well known in the art, for example, compounds of structure (III) in which $L^2$ is a leaving group displaceable by mercaptan and $R^7$ is $NH_2$ can be prepared from the corresponding compounds of structure (III) in which $R^7$ is hydrogen, by:

(i) reaction of a compound of structure (III) in which $R^7$ is hydrogen and $L^2$ is, for example, methoxy with nitric acid and sulphuric acid to give a compound of structure (III) in which $R^7$ is a nitro group. Reduction of the intermediate nitro derivative so formed, gives a compound of structure (III) in which $R^7$ is $NH_2$ and $L^2$ is methoxy. Deprotection of the group $L^2$ with, for example, boron tribromide gives a compound of structure (III) in which $L^2$ is hydroxy. The hydroxy group can then be converted to other suitable groups $L^2$ using standard procedures, for example, reaction with p-toluenesulphonyl chloride gives a compound of structure (III) in which $L^2$ is O-toluenesulphonyl; or reaction with thionyl chloride gives a compound of structure (III) in which $L^2$ is chlorine; or (ii) reaction of a compound of structure (III) in which $R^7$ is hydrogen and $L^2$ is, for example, methoxy with, for example, bromine to give a compound of structure (III) in which $R^7$ is bromine. Reaction of the intermediate so formed with ammonia gives the required compound of structure (III) in which $R^7$ is $NH_2$ and $L^2$ is methoxy. Reaction of the compound of structure (III) so formed with, for example, boron tribromide gives the corresponding compound of structure (III) in which $L^2$ is hydroxy. The group $L^2$ can then be modified by standard procedures, for example, as described in (i) above.

Compounds of structure (III) in which $R^7$ is hydrogen can themselves be prepared by methods analogous to those known in the art. For example, by reaction of a compound of structure (X)

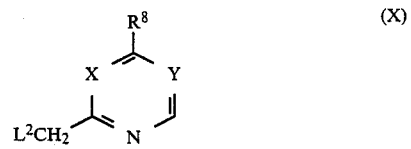

(X)

in which $R^8$ is halogen, for example chlorine or bromine, and $L^2$ is methoxy or hydroxy, with a suitable amine of structure $R^5R^6NH$ in which $R^5$ and $R^6$ are as described for structure (I).

Suitable conditions include heating in a suitable inert solvent, for example tetrahydrofuran in the presence of an excess of amine.

Compounds of structure (X) can be prepared by methods well known to those skilled in the art, for example by reaction of the corresponding compounds in which $R^8$ is hydroxy with, for example, phosphorus oxychloride to form a compound of structure (X) in which $R^8$ is chlorine.

Compounds of structure (X) in which $R^8$ is hydroxy can be prepared by reaction of an appropriately substituted amidine with an appropriately substituted β-ketoester. For example, reaction of methoxyacetamidine hydrochloride and ethyl formyl acetate sodium salt gives a compound of structure (X) in which X is nitrogen, Y is CH and $L^2$ is methoxy; and reaction of formamidine acetate and 3-keto-4-methoxybutyric acid ethyl ester gives a compound of structure (X) in which X is CH, Y is nitrogen and $L^2$ is methoxy.

Compounds of structure (III) in which $L^2$ is SH can be prepared from compounds of structure (III) in which $L^2$ is a leaving group, for example, halogen by reaction with, for example NaSH.

Compounds of structure (V) can be prepared from the corresponding compounds of structure (III); for example, compounds of structure (V) in which $X^1$ is CSCl can be prepared by reaction of a compound of structure (III) in which $L^2$ is SH with thiophosgene.

Compounds of structure (VII) can be prepared by methods analogous to those described in Roszniki Chem., 35, 475, 1961.

The compounds of structure (I) and their pharmaceutically acceptable salts inhibit exogenously and endogenously stimulated gastric acid secretion and are useful in the treatment of gastro-intestinal diseases in mammals, in particular humans. Such diseases include, for example, gastric and duodenal ulcers, and Zollinger-Ellison Syndrome.

Further, the compounds of structure (I) can be used in the treatment of other disorders where a cytoprotective and/or anti-secretory effect is desirable, for example, in patients with gastritis, NSAID induced gastritis, gastritis associated with a history of chronic and excessive alcohol consumption, gastric ulcers, acute upper gastrointestinal bleeding, for the prophylaxis of upper gastrointestinal haemmorage in patients at risk of the development of stress-related lesions of the gastric mucosa, and in the reduction of risk factors, for example gastric acidity and volume associated with pulmonary aspiration.

It is believed that, after administration to mammals, compounds of structure (I) in which n is 0 exert their anti-secretory and cytoprotective activities after conversion into compounds of structure (I) in which n is 1.

Furthermore it is believed that compounds of structure (I) in which n is 1, after administration to mammals, exert their anti-secretory activity after transformation under acid conditions into another chemically reactive species. Active species so generated from compounds of structure (I) are within the scope of the present invention.

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

Compounds of structure (I) and their pharmaceutically acceptable salts can be administered in standard manner for example, orally, parenterally, rectally, transdermally, via inhalation or via buccal administration.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compounds of structure (I) in which n is 1 are susceptible to decomposition in acid media, and thus tablets and capsules containing such compounds are preferably provided with an enteric coating to protect the compound from acid degradation in the stomach or capsules used which are inherently acid resistant. Alternatively, the enteric coating can be provided by coating pellets containing the active ingredient before filling them into the hard gelatin capsule. Suitable enteric coating materials are those well known in the art of pharmacy and include for example shellac or anionic-film forming polymers such as cellulose acetate phthalate and hydroxypropylmethyl cellulose phthalate and the like, optionally in the presence of a plasticizer.

It will be apparent to those skilled in the art that other standard techniques for enhancing the stability of such compounds can be used. The nature of such techniques will depend on the route of administration and include, for example, the formation of stable complexes with, for example β-cyclodextrin.

The compounds of structure (I) and their pharmaceutically acceptable salts which are active when administered parenterally (i.e. by injection or infusion) can be formulated as solutions or suspensions.

A composition for parenteral administration will generally consist of a solution or suspension of the active ingredient in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository composition comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

A typical transdermal formulation comprises a conventional aqueous or non-aqueous vehicle, for example, a cream, ointment lotion or paste or in the form of a medicated plaster, patch or membrane.

A typical composition for inhalation comprises a solution, suspension or emulsion that may be administered in the form of an aerosol using a conventional propellant such as dichlorodifluoromethane or trichlorofluoromethane.

Preferably the composition is in unit dose form. Each dosage unit for oral administration contains preferably from 1 to 250 mg (and for parenteral administration contains preferably from 1 to 150 mg) of a compound of the formula (I) or a pharmaceutically acceptable salt thereof calculated as the free base.

The present invention provides a method of inhibiting gastric acid secretion which comprises administering to a mammal in need thereof an effective amount of a compound of structure (I) or a pharmaceutically acceptable salt thereof.

The present invention also provides a method for the treatment of gastro-intestinal diseases and other conditions caused or exacerbated by gastric acidity which comprises administering to a mammal in need thereof an effective amount of a compound of structure (I) or a pharmaceutically acceptable salt thereof.

The daily dosage regimen for an adult patient may be, for example, an oral dose of between 1 mg and 500 mg, preferably between 1 mg and 250 mg, or an intravenous, subcutaneous, or intramuscular dose of between 1 mg and 500 mg, preferably between 1 mg and 150 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers, for example pirenzipine, prostanoids for example 16,16 dimethyl $PGE_2$ or histamine $H_2$-antagonists, for example cimetidine.

The following examples illustrate the invention. Temperatures are recorded in degrees centigrade.

EXAMPLE 1

Preparation of
5-Methoxy-2-(4-piperidino-2-pyrimidinylmethylthio)-(1H)-benzimidazole (i) A mixture of methoxyacetamidine hydrochloride (57 g) and ethyl formyl acetate sodium salt (150.5 g) in water (670 ml) were stirred at room temperature for 3 days. The volume was reduced and the solution acidified, saturated with sodium chloride and extracted with chloroform. After drying ($MgSO_4$), the extracts were stripped to a solid which was triturated with ether to give 2-methoxymethyl-4-pyrimidone (53.5 g) m.p. 125°–7°.

(ii) A mixture of 2-methoxymethyl-4-pyrimidone (1.73 g) and phosphorus oxychloride (20 ml) were heated together under reflux for 30 minutes. The mixture was stripped, ice/water added and the pH raised to 14 (NaOH). The solution was extracted with chloroform, the extracts dried ($MgSO_4$) and stripped to give 2-methoxymethyl-4-chloropyrimidine (1.72 g) as an oil which was used without further purification.

(iii) Piperidine (6.17 ml) in dichloromethane (40 ml) was added dropwise to a solution of 2-methoxymethyl-4-chloropyrimidine (4.71 g) in dichloromethane (40 ml). After standing overnight at room temperature the mixture was heated under reflux for 1 hour. After cooling the solution was washed with water, dried and stripped. The residue was chromatographed (silica gel, $CHCl_3$) to give 2-methoxymethyl-4-piperidinopyrimidine (4.49 g) as an oil.

(iv) Boron tribromide (6.1 ml) was added dropwise to a stirred solution of 2-methoxymethyl-4-piperidinopyrimidine (3.35 g) in dichloromethane (60 ml) at 0°–5° under nitrogen. After a further 30 minutes the mixture was poured onto ice, the pH raised to 13 (NaOH) and extracted with chloroform. The combined extracts were dried ($K_2CO_3$) and the volume reduced. Ether was added to give 2-hydroxymethyl-4-piperidino-pyrimidine (2.78 g) as a crystalline solid, m.p. 92°–3°.

(v) Thionyl chloride (3.01 ml) was added dropwise to a stirred solution of 2-hydroxymethyl-4-piperidinopyrimidine (2.66 g) in chloroform (20 ml) cooled in an ice/salt bath. The mixture was allowed to warm to room temperature and stirred for a further 2.5 hours. The solution was poured onto ice, the pH raised to ca. 8 (NaOH), and extracted with chloroform. The extracts were dried and stripped to give 2-chloromethyl-4-piperidino-pyrimidine (2.92 g) as an unstable oil which was used immediately.

(vi) A mixture of 2-chloromethyl-4-piperidinopyrimidine (2.89 g) and 2-mercapto-5-methoxybenzimidazole (2.46 g) in ethanol (40 ml) and 1N sodium hydroxide (15 ml) was stirred at room temperature for 16 hours. After stripping the residue was washed with water and recrystallised from acetonitrile to give 5-methoxy-2-(4-piperidino-2-pyrimidinylmethylthio)-(1H)-benzimidazole (3.5 g) m.p. 145°–147°.

EXAMPLE 2

Preparation of
5-methoxy-2-(4-piperidino-2-pyrimidinylmethylsulphinyl)-(1H)-benzimidazole A solution of m-chloroperbenzoic acid (1.69 g) in dichloromethane (25 ml) was added to a stirred solution of 5-methoxy-2-[4-piperidino-2-pyrimidinylmethylthio]-(1H) benzimidazole (3.48 g) in dichloromethane (75 ml) cooled to between −30° and −35°. After 1.5 hours at −20° a further quantity of m-chloroperbenzoic acid (0.34 g) was added. After a further 30 minutes ammonia was passed through the reaction mixture and the precipitated solid filtered off. The filtrate was washed with aqueous sodium carbonate, which was back washed with chloroform. The combined organic phases were dried ($K_2CO_3$) stripped and the residue purified by column chromatography (silica gel, 2% MeOH-$NH_3$/$CHCl_3$) to give 5-methoxy-2-(4-piperidino-2-pyrimidinylmethylsulphinyl)-(1H)-benzimidazole (3.28 g) as an oil.

EXAMPLE 3

Preparation of
5-methoxy-2-(4-piperidino-2-pyrimidinylmethylsulphinyl)-(1H)-benzimidazole Calcium Salt 2.5 $H_2O$ 5-Methoxy-2-(4-piperidino-2-pyrimidinylmethylsulphinyl)-(1H)-benzimidazole (3.28 g) was partitioned between dichloromethane (20 ml), water (20 ml) and 1N sodium hydroxide (8.83 ml). The organic phase was separated off and the aqueous phase filtered and treated with a solution of calcium chloride (6H$_2$O, 0.97 g) in water (10 ml). The precipitate was filtered off and dried to give the title compound (1.89 g) m.p. 204°–6° (dec).
C$_{36}$H$_{40}$CaN$_{10}$O$_4$S$_2$.2.5H$_2$O:
Found: C, 52.30; H, 5.43; N, 16.71; S, 7.71%:
Requires: C, 52.34; H, 5.19; N, 16.96; S, 7.76%.

EXAMPLE 4

Preparation of 5-methoxy-2-(4-morpholino-2-pyrimidinyl methylthio)-(1H)-benzimidazole (i) A solution of morpholine (12.67 g) and 2-methoxymethyl-4-chloropyrimidine (7.69 g) in tetrahydrofuran (100 ml) was heated under reflux for 1 hour. On cooling, the mixture was treated with water (100 ml), the pH adjusted to 8 (conc HCl) and extracted with chloroform. After drying (K$_2$CO$_3$) the extracts were stripped, and the residue purified by chromatography (silica gel, CHCl$_3$/methanol) to give 2-methoxymethyl-4-morpholinopyrimidine (5.4 g) as an oil.

(ii) A solution of boron tribromide (9.02 ml) in dichloromethane (100 ml) was added dropwise to a stirred solution of 2-methoxymethyl-4-morpholinopyrimidine (4.99 g) in dichloromethane (50 ml) at −25° under nitrogen. After 15 minutes the mixture was allowed to warm to 0°–5°, and left to stand for 2 hours at this temperature. After pouring onto ice, the pH was raised to 14 (NaOH), and the organic phase separated off. The aqueous phase was further extracted with chloroform, and the combined extracts dried (K$_2$CO$_3$) and stripped. The residue was triturated with ether to give 2-hydroxymethyl-4-morpholinopyrimidine (3.16 g) as a crystalline solid, m.p. 76°–8°.

(iii) Thionyl chloride (3.4 ml) was added dropwise to a stirred solution of 2-hydroxymethyl-4-morpholinopyrimidine in chloroform (30 ml) cooled in an ice bath. The mixture was allowed to warm to room temperature and left to stand for a further 1.5 hours. The solution was reduced to low volume, and ether added with stirring to give 2-chloromethyl-4-morpholinopyrimidine hydrochloride (3.8 g) as a crystalline solid, m.p. 214°–6°.

(iv) 5N sodium hydroxide (6.42 ml) was added dropwise to a stirred mixture of 2-chloromethyl-4-morpholinopyrimidine hydrochloride (3.65 g) and 2-mercapto-5-methoxybenzimidazole (2.63 g). Stirring was continued for 1.5 hours and the mixture was allowed to stand for a further 16 hours. After stripping, the solid residue was washed with water and recrystallised from acetonitrile to give 5-methoxy-2-(4-morpholino-2-pyrimidinylmethylthio)-(1H)-benzimidazole (4.09 g), m.p. 188°–92°.

EXAMPLE 5

Preparation of 5-methoxy-2-(4-morpholino-2-pyrimidinyl-methylsulphinyl)-(1H)-benzimidazole Substituting 5-methoxy-2-(4-morpholino-2-pyrimidinylmethylthio)-(1H)-benzimidazole (3.53 g) for 5-methoxy-2-(4-piperidino-2-pyrimidinylmethylthio)-(1H)-benzimidazole and using corresponding molar proportions of the other reagents in the method of Example 2 gave 5-methoxy-2-(4-morpholino-2-pyrimidinylmethylsulphinyl)-(1H)-benzimidazole (2.58 g), m.p. 154-6 (dec), from acetonitrile.
C$_{17}$H$_{19}$N$_5$O$_3$S:
Found: C, 54.85; H, 5.11; N, 18.64; S, 8.61.
Requires: C, 54.68; H, 5.13; N, 18.76; S, 8.59.

EXAMPLE 6

Preparation of 5-methoxy-2-(4-pyrrolidino-2-pyrimidinylmethylthio)-(1H)-benzimidazole (i) Substituting pyrrolidine (8.51 ml) for piperidine and using corresponding molar proportions of the other reagents in the method of Example 1(iii), gave 5-methoxy-2-(4-pyrrolidino-2-pyrimidinylmethylthio)-(1H)-benzimidazole (8.49 g) as an oil.

(ii) Substituting 2-methoxymethyl-4-pyrrolidinopyrimidine (8.31 g) for 2-methoxymethyl-4-piperidinopyrimidine and using corresponding molar proportions of the other reagents in the method of Example 1(iv), gave 2-hydroxymethyl-4-pyrrolidinopyrimidine (6.72 g), m.p. 114°–6°, from ether.

(iii) Substituting 2-hydroxymethyl-4-pyrrolidinopyrimidine (3.0 g) for 2-hydroxymethyl-4-morpholino pyrimidine and using corresponding molar proportions of the other reagents in the method of Example 4(iii), gave 2-chloromethyl-4-pyrrolidino-pyrimidine hydrochloride (3.72 g), m.p. 186°–9°.

(iv) Substituting 2-chloromethyl-4-pyrrolidinopyrimidine hydrochloride (3.61 g) for 2-chloromethyl-4-morpholino-pyrimidine hydrochloride and using corresponding molar proportions of the other reagents in the method of Example 4(iv), gave 5-methoxy-2-(4-pyrrolidino-2-pyrimidinylmethylthio)-(1H)-benzimidazole (4.03 g), m.p. 199°–202°, from ethanol.

EXAMPLE 7

Preparation of 5-methoxy-2-(4-pyrrolidino-2-pyrimidinylmethylsulphinyl)-(1H)-benzimidazole Substituting 5-methoxy-2-(4-pyrrolidino-2-pyrimidinyl-methylthio)-(1H)-benzimidazole (3.92 g) for 5-methoxy-2-(4-piperidino-2-pyrimidinylmethylthio)-(1H)-benzimidazole and using corresponding molar proportions of the other reagents in the method of Example 2 gave 5-methoxy-2-(4-pyrrolidino-2-pyrimidinylmethylsulphinyl)-(1H)-benzimidazole (2.88 g), m.p. 175°–7° (dec) from acetonitrile.
C$_{17}$H$_{19}$N$_5$O$_2$S:
Found: C, 57.01; H, 5.35; N, 19.50; S, 9.08.
Requires: C, 57.12; H, 5.36; N, 19.59; S, 8.97.

EXAMPLE 8

Preparation of 5-methoxy-2-(4-dimethylamino-2-pyrimidinyl-methylthio)-(1H)-benzimidazole (i) A 33% w/w solution of dimethylamine in ethanol (45 ml) was added dropwise to a stirred solution of 2-methoxymethyl-4-chloropyrimidine (7.54 g) in ethanol (100 ml), cooled over an ice bath. The mixture was allowed to warm to room temperature, and left to stand for 16 hours. After stripping, the residue was treated with water (100 ml), and extracted with chloroform. The extracts were dried (K$_2$CO$_3$) and stripped to give 2-methoxymethyl-4-dimethylaminopyrimidine (7.41 g) as an oil.

(ii) Substituting 2-methoxymethyl-4-dimethylaminopyrimidine (7.2 g) for 2-methoxymethyl-4-piperidinopyrimidine and using corresponding molar proportions of the other reagents in the method of Example 1(iv), gave 2-hydroxymethyl-4-dimethylaminopyrimidine (5.7 g), m.p. 83°–4°, from ether.

(iii) Substituting 2-hydroxymethyl-4-dimethylaminopyrimidine (5.55 g) for 2-hydroxymethyl-4-morpholinopyrimidine and using corresponding molar proportions of the other reagents in the method of Example 4(iii), gave 2-chloromethyl-4-dimethylaminopyrimidine hydrochloride (7.39 g), m.p. 204°–6° from ether.

(iv) Substituting 2-chloromethyl-4-dimethylaminopyrimidine hydrochloride (3.7 g) for 2-chloromethyl-4-morpholinopyrimidine hydrochloride and using corresponding molar proportions of the other reagents in the method of Example 4(iv), gave 5-methoxy-2-(4-dimethylamino-2-pyrimidinylmethylthio)-(1H)-benzimidazole (4.41 g), m.p. 182°–3°, from ethanol.

EXAMPLE 9

Preparation of
5-methoxy-2-(4-dimethylamino-2-pyrimidinylmethylsulphinyl)-(1H)-benzimidazole Substituting 5-methoxy-2-(4-dimethylamino-2-pyrimidinylmethylthio)-(1H)-benzimidazole (4.25 g) for 5-methoxy-2-(4-piperidino-2-pyrimidinylmethylthio)-(1H)-benzimidazole and using corresponding molar proportions of the other reagents in the method of Example 2 gave 5-methoxy-2-(4-dimethylamino-2-pyrimidinylmethylsulphinyl)-(1H)-benzimidazole (2.67 g), m.p. 138°–40° (dec) from acetonitrile.

Found: C, 54,46; H, 4.97; N, 21.07; S, 9.56.
Requires: C, 54.36; H, 5.17; N, 21.13; S, 9.68.

EXAMPLE 10

Preparation of
5-methoxy-2-(5-methyl-6-piperidino-4-pyrimidinylmethylthio)-(1H)-benzimidazole (i) 2-Methyl-3-keto-4-methoxybutyric acid ethyl ester (60 g) and formamidine acetate (39.06 g) were dissolved in methanol (150 ml) and treated, under nitrogen, with a sodium methoxide solution, prepared from sodium (17.42 g) and methanol (225 ml). The mixture was stirred at 50° for 23 hours, stripped, water added and the pH lowered to 7 (HCl). The solution was extracted with chloroform, extracts dried (MgSO$_4$) and stripped to a residue, which was triturated with diethyl ether to give 4-methoxymethyl-5-methyl-6-hydroxypyrimidine, 38.72 g, m.p. 139°–140°.

(ii) 4-Methoxymethyl-5-methyl-6-hydroxypyrimidine (38.40 g) was stirred with phosphorus oxychloride (275 ml) at room temperature for 24 hours. The mixture was stripped, ice/water added and the pH raised to 11.5 (NaOH). The solution was extracted with chloroform, extracts dried (MgSO$_4$) and stripped to give 4-methoxymethyl-5-methyl-6-chloropyrimidine, 38.23 g, as an oil, which solidified on cooling to 5° (m.p. 37°–38°). It was used without further purification.

(iii) Piperidine (15 ml) in tetrahydrofuran (40 ml) was added dropwise to a solution of 4-methoxymethyl-5-methyl-6-chloropyrimidine (5 g) in tetrahydrofuran (40 ml). The mixture was heated under reflux for 7 hours and then allowed to stand overnight at room temperature. It was filtered, stripped, and water added to the residual oil. The pH was lowered to 7.5 (HCl) and extracted with chloroform. Extracts were dried (K$_2$CO$_3$) and stripped to give 4-methoxymethyl-5-methyl-6-piperidinopyrimidine, 6.08 g, as an oil, which solidified on cooling to 5° (m.p. 45°–47°). It was used without further purification.

(iv) Boron tribromide (8.9 ml) in dichloromethane (25 ml) was added dropwise, under nitrogen, to a stirred solution of 4-methoxymethyl-5-methyl-6-piperidinopyrimidine (5 g) in dichloromethane (100 ml) at 0°–5°. After a further 2 hours the mixture was poured onto ice, the pH raised to 13 (NaOH) and extracted with chloroform. Extracts were dried (K$_2$CO$_3$) and stripped to a residue, which was triturated with diethyl ether to give 4-hydroxymethyl-5-methyl-6-piperidinopyrimidine, 3.80 g, as a crystalline solid, m.p. 79°–81°.

(v) Thionyl chloride (4.5 ml) in chloroform (30 ml) was added dropwise to a stirred solution of 4-hydroxymethyl-5-methyl-6-piperidinopyrimidine (4.24 g) in chloroform (30 ml) cooled in an ice-salt bath. The mixture was allowed to warm to room temperature and stirred for a further 22 hours. The solution was stripped to a residual glass which was triturated with diethyl ether to give 4-chloromethyl-5-methyl-6-piperidinopyrimidine hydrochloride, 5.24 g, m.p. 182°–184°.

(vi) A mixture of 4-chloromethyl-5-methyl-6-piperidino pyrimidine hydrochloride (4.63 g) and 2-mercapto-5-methoxybenzimidazole (3.18 g) in ethanol (180 ml) were heated at 50° for 5 hours. The solution was stripped to a residual glass, to which water was added, the pH raised to 13 (NaOH), and extracted with chloroform. Extracts were dried (K$_2$CO$_3$) and stripped to a residual glass which crystallised from ethyl acetate to give 5-methoxy-2-(5-methyl-6-piperidino-4-pyrimidinylmethylthio)-(1H)-benzimidazole, 5.67 g, m.p. 94°–96°.

EXAMPLE 11

Preparation of
5-methoxy-2-(5-methyl-6-piperidino-4-pyrimidinylmethylsulphinyl)-(1H)-benzimidazole A solution of m-chloroperbenzoic acid (2.16 g) in dichloromethane (40 ml) was added to a stirred solution of 5-methoxy-2-(5-methyl-6-piperidino-4-pyrimidinylmethylthio)-(1H)-benzimidazole (4.0 g) in dichloromethane (110 ml) cooled to between −40° and −50°. After a further hour at −40°, ammonia was passed through the reaction mixture and the precipitated solid filtered off. The filtrate was stripped, and the residual glass triturated with acetonitrile to give 5-methoxy-2-(5-methyl-6-piperidino-4-pyrimidinylmethylsulphinyl)-(1H)-benzimidazole 2.66 g, m.p. 87°–89°.

Found: C, 58.22; H, 5.87; N, 17.78; S, 8.43.
Requires: C, 57.93; H, 6.12; N, 17.78; S, 8.14.

EXAMPLE 12

Preparation of
5-methoxy-2-(5-methyl-6-pyrrolidino-4-pyrimidinylmethylthio)-(1H)-benzimidazole (i) Substituting pyrrolidine (12.20 ml) for piperidine, 1,4-dioxan as solvent for tetrahydrofuran, and using corresponding molar proportions of the other reagents, in the method of Example 10(iii), gave 4-methoxymethyl-5-methyl-6-pyrrolidinopyrimidine, 5.52 g, as an oil. It was used without further purification.

(ii) Substituting 4-methoxymethyl-5-methyl-6-pyrrolidino pyrimidine (5.4 g) for 4-methoxymethyl-5-methyl-6-piperidinopyrimidine and using corresponding molar proportions of the other reagents in the method of Example 10(iv), gave 4-hydroxymethyl-5-methyl-6-pyrrolidinopyrimidine, 4.11 g, m.p. 112°–114°, from diethyl ether.

(iii) Substituting 4-hydroxymethyl-5-methyl-6-pyrolidino pyrimidine (3.90 g) for 4-hydroxymethyl-5-methyl-6-piperidinopyrimidine and using corresponding molar proportions of the other reagents in the method of Example 10(v), gave 4-chloromethyl-5-methyl-6-pyrrolidinopyrimidine hydrochloride, 4.88 g, m.p. 173°–175°.

(iv) Substituting 4-chloromethyl-5-methyl-6-pyrrolidinopyrimidine hydrochloride (4.80 g) for 4-chloromethyl-5-methyl- 6-piperidinopyrimidine hydrochloride in the method of Example 10(vi) and using corresponding molar proportions of other reagents, gave 5-methoxy-2-(5-methyl-6-pyrrolidino-4-pyrimidinylmethylthio)-(1H)-benzimidazole, 5.78 g, m.p. 104°–106°, from acetonitrile.

EXAMPLE 13

Preparation of 5-methoxy-2-(5-methyl-6-pyrrolidino-4-pyrimidinylmethylsulphinyl)-(1H)-benzimidazole Substituting 5-methoxy-2-(5-methyl-6-pyrrolidino-4-pyrimidinylmethylthio)-(1H)-benzimidazole for 5-methoxy-2-(5-methyl-6-piperidino-4-pyrimidinylmethylthio)-(1H)benzimidazole and using corresponding molar proportions of other reagents in the method of Example 11 gave 5-methoxy-2-(5-methyl-6-pyrrolidino-4-pyrimidinylmethylsulphinyl)-(1H)-benzimidazole 3.33 g, m.p. 144°–146° (dec), from acetonitrile.

$C_{18}H_{21}N_5O_2S$:
Found: C, 58.14; H, 5.70; N, 18.66; S, 8.57.
Require: C, 58.20; H, 5.70; N, 8.85; S, 8.63.

EXAMPLE 14

Preparation of 5-methoxy-2-(5-methyl-6-morpholino-4-pyrimidinylmethylthio)-(1H)-benzimidazole (i) Substituting morpholine (12.9 ml) for piperidine, 1,4-dioxan as solvent for tetrahydrofuran, and using corresponding molar proportions of the other reagents, in the method of Example 10(iii), gave 4-methoxymethyl-5-methyl-6-morpholinopyrimidine, 5.81 g, as an oil. It was used without further purification.

(ii) Substituting 4-methoxymethyl-5-methyl-6-morpholinopyrimidine, (5.77 g), for 4-methoxymethyl-5-methyl-6-piperidinopyrimidine and using corresponding molar proportions of the other reagents in the method of Example 10(iv), gave 4-hydroxymethyl-5-methyl-6-morpholinopyrimidine, 3.46 g, m.p. 66°–68°, from petroleum ether (40/60).

(iii) Substituting 4-hydroxymethyl-5-methyl-6-morpholinopyrimidine (3.35 g) for 4-hydroxymethyl-5-methyl-6-piperidinopyrimidine and using corresponding molar proportions of the other reagents in the method of Example 10(v) gave 4-chloromethyl-5-methyl-6-morpholinopyrimidine hydrochloride, 4.22 g, m.p. 188°–190° (dec), from diethyl ether.

(iv) Substituting 4-chloromethyl-5-methyl-6-morpholinopyrimidine hydrochloride (4.17 g) for 4-chloromethyl-5-methyl-6-piperidinopyrimidine hydrochloride and using corresponding molar proportions of the other reagents in the method of Example 10(vi) gave 5-methoxy-2-(5-methyl-6-morpholino-4-pyrimidinylmethylthio)-(1H)-benzimidazole, 4.51 g, m.p. 129°–131°, from ethyl acetate.

EXAMPLE 15

Preparation of 5-methoxy-2-(5-methyl-6-morpholino-4-pyrimidinylmethylsulphinyl)-(1H)-benzimidazole Substituting 5-methoxy-2-(5-methyl-6-morpholino-4-pyrimidinylmethylthio)-(1H)-benzimidazole for 5-methoxy-2-(5-methyl-6-piperidino-4-pyrimidinylmethylthio)-(1H)benzimidazole and using corresponding molar proportions of other reagents in the method of Example 11 gave 5-methoxy-2-(5-methyl-6-morpholino-4-pyrimidinylmethylsulphinyl)-(1H)-benzimidazole, 2.67 g, m.p. 176°–178° (dec), from acetonitrile.

$C_{18}H_{21}N_5O_3S$:
Found: C, 55.74; H, 5.40; N, 17.96; S, 8.17.
Requires: C, 55.80; H, 5.46; N, 18.08; S, 8.28.

EXAMPLE 16

Preparation of 5-methoxy-2-(5-methyl-6-dimethylamino-4-pyrimidinylmethylthio)-(1H)-benzimidazole (i) Substituting 4-methoxymethyl-5-methyl-6-chloropyrimidine (5.0 g) for 2-methoxymethyl-4- chloropyrimine, and using corresponding molar proportions of the other reagents, in the method of Example 8(i), gave 4-methoxymethyl-5-methyl-6-dimethylaminopyrimidine, 4.77 g, as an oil. It was used without further purification.

(ii) Substituting 4-methoxymethyl-5-methyl-6-dimethylaminopyrimidine (4.7 g) for 4-methoxymethyl-5-methyl-6-piperidinopyrimidine and using corresponding molar proportions of the other reagents in the method of Example 10(iv), gave 4-hydroxymethyl-5-methyl-6-dimethylaminopyrimidine, 3.52 g, m.p. 46°–48°, from petroleum ether (40–60).

(iii) Substituting 4-hydroxymethyl-5-methyl-6-dimethylaminopyrimidine (3.35 g) for 4-hydroxymethyl-5-methyl-6-piperidinopyrimidine and using corresponding molar proportions of the other reagents in the method of Example 10(v), gave 4-chloromethyl-5-methyl-6-dimethylaminopyrimidine hydrochloride, 4.30 g, m.p. 176°–178°, from diethyl ether.

(iv) Substituting 4-chloromethyl-5-methyl-6-dimethylaminopyrimidine hydrochloride (4.20 g) for 4-chloromethyl-5-methyl-6-piperidinopyrimidine hydrochloride and using corresponding molar proportions of the other reagents in the method of Example 10, gave, after chromatography (silica gel, CHCl₃/MeOH), 5-methoxy-2-(5-methyl-6-dimethylamino-4-pyrimidinylmethylthio)-(1H)-benzimidazole, 5.28 g, as a glass.

EXAMPLE 17

Preparation of 5-methoxy-2-(5-methyl-6-dimethylamino-4-pyrimidinylmethylsulphinyl)-(1H)-benzimidazole Substituting 5-methoxy-2-(5-methyl-6-dimethylamino-4-pyrimidinylmethylthio)-(1H)-benzimidazole (3.86 g) for 5-methoxy-2-(5-methyl-6-piperidino-4-pyrimidinylmethylthio)-(1H)-benzimidazole and using corresponding molar proportions of other reagents in the method of Example 11, gave 5-methoxy-2-(5-methyl-6-dimethylamino-4-pyrimidinyl-methylsulphinyl)-(1H)-benzimidazole, 3.36 g, m.p. 141°–143° (dec), from acetonitrile.

$C_{16}H_{19}N_5O_2S$:
Found: C, 55.43; H, 5.64; N, 20.14; S, 9.25.
Requires: C, 55,63; H, 5.54; N, 20.27; S, 9.28.

EXAMPLE 18

Preparation of
5-methoxy-2-(6-piperidino-4-pyrimidinylmethylthio)-(1H)-benzimidazole (i) Substituting 3-keto-4-methoxybutyric acid ethyl ester (35.75 g) for 2-methyl-3-keto-4-methoxybutyric acid ethyl ester and using corresponding molar proportions of the other reagents in the method of Example 10(i), gave 4-methoxymethyl-6-hydroxypyrimidine, 13.35 g, m.p. 159°–161°, from diethyl ether.

(ii) Substituting 4-methoxymethyl-6-hydroxypyrimidine (15.40 g) for 4-methoxymethyl-5-methyl-6-hydroxypyrimidine and using corresponding molar proportions of the other reagents in the method of Example 10(ii), gave 4-methoxymethyl-6-chloropyrimidine, 16.77 g, m.p. 34°–36°. It was used without further purification.

(iii) Substituting 4-methoxymethyl-6-chloropyrimidine (4.0 g) for 4-methoxymethyl-5-methyl-6-chloropyrimidine and using corresponding molar proportions of the other reagents in the method of Example 10(iii) gave 4-methoxymethyl-6-piperidino-pyrimidine, 4,88 g, as an oil. It was used without further purification.

(iv) Substituting 4-methoxymethyl-6-piperidinopyrimidine (4.70 g) for 4-methoxymethyl-5-methyl-6-piperidinopyrimidine and using corresponding molar proportions of the other reagents in the method of Example 10(iv) gave 4-hydroxymethyl-6-piperidinopyrimidine, 3.67 g, m.p. 70°–72°, from diethyl ether.

(v) Substituting 4-hydroxymethyl-6-piperidinopyrimidine (3.56 g) for 4-hydroxymethyl-5-methyl-6-piperidinopyrimidine and using corresponding molar proportions of the other reagents in the method of Example 10(v) gave 4-chloromethyl-6-piperidinopyrimidine hydrochloride, 4.55 g, m.p. 187°–189°, from diethyl ether.

(vi) Substituting 4-chloromethyl-6-piperidinopyrimidine hydrochloride (4.47 g) for 4-chloromethyl-5-methyl-6-piperidinopyrimidine hydrochloride and using corresponding molar proportions of the other reagents in the method of Example 10(vi) gave, after chromatography (silica gel, $CHCl_3/MeOH$), 5-methoxy-2-(6-piperidino-4-pyrimidinylmethylthio)-(1H)-benzimidazole, 5.72 g, as a glass.

EXAMPLE 19

Preparation of
5-methoxy-2-(6-piperidino-4-pyrimidinylmethylsulphinyl)-(1H)-benzimidazole Substituting 5-methoxy-2-(6-piperidino-4-pyrimidinylmethylthio)-(1H)-benzimidazole (4.12 g) for 5-methoxy-2-(5-methyl-6-piperidino-4-pyrimidinylmethylthio)-(1H)-benzimidazole and using corresponding molar proportions of other reagents in the method of Example 2, gave 5-methoxy-2-(6-piperidino-4-pyrimidinylmethylsulphinyl)-(1H)-benzimidazole, 2.44 g, m.p. 98°–101°, from ethyl acetate.

$C_{18}H_{21}N_5O_2S$ 0.33 EtOAc 0.18$H_2O$:
Found: C, 57.44; H, 5.93; N, 17.29; S, 7.90.
Requires: C, 57,47; H, 5.99; N, 17.36; S, 7.95.

EXAMPLE 20

Preparation of
5-methoxy-2-(6-pyrrolidino-4-pyrimidinylmethylthio)-(1H)-benzimidazole (i) Substituting pyrrolidine (10.4 ml) for piperidine and using corresponding molar proportions of the other reagents in the method of Example 18(iii), gave 4-methoxymethyl-6-pyrrolidino pyrimidine, 4.65 g, as an oil. It was used without further purification.

(ii) Substituting 4-methoxymethyl-6-pyrrolidinopyrimidine (4.60 g) for 4-methoxymethyl-5-methyl-6-piperidinopyrimidine and using corresponding molar proportions of the other reagents in the method of Example 10(iv), gave 4-hydroxymethyl-6-pyrrolidinopyrimidine, 3.84 g, m.p. 136°–139°, from diethyl ether.

(iii) Substituting 4-hydroxymethyl-6-pyrrolidinopyrimidine for 4-hydroxymethyl-5-methyl-6-piperidinopyrimidine and using corresponding molar proportions of the other reagents in the method of Example 10(v), gave 4-chloromethyl-6-pyrrolidinopyrimidine hydrochloride, 4.66 g, m.p. 180°–182° (dec), from diethyl ether.

(iv) Substituting 4-chloromethyl-6-pyrrolidinopyrimidine hydrochloride for 4-chloromethyl-5-methyl-6-piperidinopyrimidine hydrochloride and using corresponding molar proportions of the other reagents in the method of Example 10(vi), gave 5-methoxy-2-(6-pyrrolidino-4-pyrimidinylmethylthio)-(1H)-benzimidazole, 6.41 g, as a glass.

EXAMPLE 21

Preparation of
5-methoxy-2-(6-pyrrolidino-4-pyrimidinylmethylsulphinyl)-(1H)-benzimidazole Substituting 5-methoxy-2-(6-pyrrolidino-4-pyrimidinylmethylthio)-(1H)-benzimidazole (4.0 g) for 5-methoxy-2-(5-methyl-6-piperidino-4-pyrimidinylmethylthio)-(1H)-benzimidazole and using corresponding molar proportions of other reagents in the method of Example 11, gave 5-methoxy-2-(6-pyrrolidino-4-pyrimidinylmethylsulphinyl)-(1H)-benzimidazole, 2.79 g, m.p. 95°–97° (dec), from acetonitrile.

$C_{17}H_{19}N_5O_2S$ 0.04$CH_2CL_2$ 0.67$H_2O$:
Found: C, 55.01; H, 5.68; N, 18.72; S, 8.54.
Requires: C, 54.85; H, 5.52; N, 18.78; S, 8.59.

EXAMPLE 22

Preparation of
5-methoxy-2-(6-dimethylamino-4-pyrimidinylmethylthio)-(1H)-benzimidazole (i) Substituting 4-methoxymethyl-6-chloropyrimidine (4.0 g) for 2-methoxymethyl-4-chloropyrimidine, and using corresponding molar proportions of the other reagents, in the method of Example 8(i), gave 4-methoxymethyl-6-dimethylaminopyrimidine, 4.1 g, as a low melting solid, m.p. 42°–44°. It was used without further purification.

(ii) Substituting 4-methoxymethyl-6-dimethylaminopyrimidine (4.06 g) for 4-methoxymethyl-5-methyl-6-piperidinopyrimidine and using corresponding molar proportions of the other reagents in the method of Example 10(iv), gave 4-hydroxymethyl-6- dimethylaminopyrimidine, 3.05 g, m.p. 137°–139°, from diethyl ether.

(iii) Substituting 4-hydroxymethyl-6-dimethylaminopyrimidine (2.95 g) for 4-hydroxymethyl-5-methyl-6-piperidinopyrimidine and using corresponding molar proportions of the other reagents in the method of Example 10(v), gave 4-chloromethyl-6-dimethylaminopyrimidine hydrochloride, 3.97 g, m.p. 225°–226° from diethyl ether.

(iv) Substituting 4-chloromethyl-6-dimethylaminopyrimidine hydrochloride (3.90 g) for 4-chloromethyl-5-methyl-6-piperidinopyrimidine hydrochloride and using corresponding molar proportions of the other reagents in the method of Example 10(vi), gave 5-methoxy-2-(6-dimethylamino-4-pyrimidinylmethylthio)-(1H)-benzimidazole, 5.80 g, as a glass.

EXAMPLE 23

Preparation of 5-methoxy-2-(6-dimethylamino-4-pyrimidinylmethylsulphinyl)-(1H)-benzimidazole Substituting 5-methoxy-2-(6-dimethylamino-4-pyrimidinylmethylthio)-(1H)-benzimidazole (4.0 g) for 5-methoxy-2-(5-methyl-6-piperidino-4-pyrimidinylmethylthio)-(1H)-benzimidazole and using corresponding molar proportions of other reagents in the method of Example 11, gave 5-methoxy-2-(6-dimethylamino-4-pyrimidinylmethyl-sulphinyl)-(1H)-benzimidazole, 3.06 g, m.p. 104°–106°, from acetonitrile.

$C_{15}H_{17}N_5O_2S$ 0.23 $CH_3CN$:
Found: C, 54.45; H, 5.33; N, 21.51; S, 9.23.
Requires: C, 54,48; H, 5.24; N, 21.50; S, 9.41.

EXAMPLE A

A tablet for oral administration is prepared by combining

|  | Mg/Tablet |
| --- | --- |
| Compound of structure (I) | 100 |
| Mannitol | 153 |
| Starch | 33 |
| polyvinylpyrrolidone | 12 |
| microcrystalline cellulose | 30 |
| magnesium stearate | 2 |
|  | 330 mg | into a 9 mm tablet. If the active ingredient is a compound of structure (I) in which n is 1 then the tablet is provided with an enteric coating.

EXAMPLE B

A pellet formulation for oral administration may be prepared by formulating the following into pellets by standard techniques

|  | % w:w |
| --- | --- |
| Compound of structure (I) | 80 |
| microcrystalline cellulose | 10 |
| sodium carboxymethylcellulose | 2 |
| lactose | 8 |

If the active ingredient is a compound of structure (I) in which n is 1, the pellets are first enteric coated before being filled into hard gelatin capsules.

EXAMPLE C

An injection for parenteral administration is prepared by combining

|  | % w:w |
| --- | --- |
| Compound of example 1 | 1–5 |
| polyethylene glycol | 40 |
| ethanol | 10 |
| water for injection EP to | 100 |

The solution is then sterilised by an appropriate method and sealed into 2 ml and 5 ml ampoules and vials.

EXAMPLE D

A reconstitutable lyophilisate for parenteral administration is prepared from:

|  | % w:w |
| --- | --- |
| Compound of structure (I) as a salt | 1–5 |
| Mannitol | 3 |
| NaCl | sufficient to make reconstituted solution isotonic |
| water to | 100 |

The solution is sterilised by an appropriate method, 5 ml portions dispensed into 15 ml vials and the solution lyophilised. The lyophilisate can be reconstituted with a suitable carrier, for example water, a buffered solution or a co-solvent mixture.

Biological Data

Inhibition of gastric acid secretion is demonstrated by the following test procedures:

A. $K^+$ Stimulated ATPase Activity

The effects of a single high concentration (1 mM) of a compound of structure (I) on $H^+$-$K^+$-ATPase were determined at pH 6.1 and pH 7.4. Preferred compounds of structure (I) were also tested over a range of concentrations to determine $IC_{50}$ values at pH 6.1 and 7.4.

(i) Preparation of Lyophilised Gastric Vesicles ($H^+$-$K^+$-ATPase)

$H^+$-$K^+$-ATPase was prepared from the lyophilised gastric vesicles of pig fundic mucosa after the method of Saccomani et. al. (Biochem and Biophys. Acta., 465, 311, 1977).

(ii) $K^+$ Stimulated ATPase Activity

Compounds of structure (I) were pre-incubated with $H^+$-$K^+$-ATPase preparation 30 μg protein/ml from (i) in 10 mM Pipes/Tris buffer pH 6.1 and pH 7.4.

After 30 minutes at 37° the pre-incubation was diluted 5-fold with assay buffer to start the ATPase reaction. The conditions in the assay are 100 mM Pipes/Tris, 2 mM $MgCl_2$, 10 mM KCl, 5 μg/ml nigericin, 2 mM Na ATP, pH 7.0. After an incubation at 37° for 15 minutes the inorganic phosphate released was determined by the method of Yoda & Hokin (Biochem. Biophys. Res. Com. 40, 880, 1970). Nigericin was dissolved in methanol, which at the final concentration of 0.5%, did not affect the enzyme activity.

The effect of the same concentration of compound of structure (I) (pre-incubated with $H^+$-$K^+$-ATPase preparation at pH 7.4 as described above) on the recovery of 100 nmole of inorganic phosphate was also determined.

Compounds of structure (I) were initially dissolved in dimethyl sulphoxide, polyethylene glycol (Type 400) or Pipes/Tris buffer. None of these solvents affects $K^+$-ATPase activity at the concentrations used.

(iii) Results

The compound of Example 3 was found to inhibit potassium stimulated $H^+$-$K^+$ATPase at pH6.1 and 7.4.

B. Aminopyrine (AP) accumulation in intact gastric glands

The effect of a single concentration (100 μm) of a compound of structure (I) on dibutyryl cAMP stimulated AP metabolism in rabbit intact gastric glands was determined. Preferred compounds of structure (I) were tested over a range of concentrations to determine the $IC_{50}$ value.

(i) Preparation of intact gastric glands.

Intact gastric glands were prepared from New Zealand white rabbits by the method of Berghindh et al. (Acta. Physio: Scand. 96, 150, 1976). Gastric mucosal scrapings were digested at 37° C. for 45–60 min. with Collagenase (100 U, Type 1, Sigma), and glands harvested by coarse filtration and sedimentation.

(ii) AP accumulation

Test compound was incubated with glands and 300 μM dibutyryl cAMP for 30 minutes at 37° C. Incubating medium contained 132.5 mM NaCl, 5.4 mM KCl, 1.0 mM $NaH_2PO_4$, 5.0 mM $Na_2HPO_4$, 1.2 mM $MgSO_4$, 1.0 mM $CaCl_2$, 11.1 mM glucose, 2.0 mg/ml rabbit albumin, 10 μg/ml phenol red, approximately 0.3 μM[$^{14}$C] aminopyrine (110 mCi/mmole), pH 7.4.

After incubation, glands were centrifuged and the supernatant removed. The glands were dried, weighed and dissolved in NaOH. The distribution of radioactivity between the supernatant and glands is then used to calculate the AP ratio after the method of Berglindh et al. (Acta. Physiol. Scand. 97, 401, 1976).

The $IC_{50}$ value is the amount of compound required to inhibit the stimulated accumulation of aminopyrine by 50%.

(iii) Results

| Compound of Example | $IC_{50}$ (μM) |
|---|---|
| 3 | 16.00 |
| 7 | 2.44 |
| 9 | 1.20 |
| 11 | 6.15 |
| 13 | 0.32 |
| 15 | 5.00 |
| 17 | 3.33 |
| 19 | 2.64 |

C. Rat: Lumen perfused stomach (histamine stimulated gastric acid secretion).

Using a modification of the procedure described by Ghosh and Schild (Br. J. Pharmacology, 13, 54, 1958), $ED_{50}$ values after either intraduodenal (i.d) or intravenous (i.v) administration were obtained as follows:

| Compound of Example | Route of Administration | $ED_{50}$ μmol/kg |
|---|---|---|
| 3 | i.v. | 1.4 |
| 9 | i.d. | 2.4 |
| 13 | i.d. | 2.8 |

No overt signs of toxicity were observed in any of the foregoing tests.

What is claimed is:

1. A compound of structure (I)

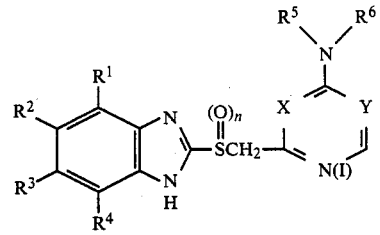

in which

R$^1$ and R$^4$ are the same or different and are each hydrogen, $C_{1-6}$alkyl, halogen, trifluoromethyl, $C_{1-6}$alkoxy, $C_{1-6}$alkanoyl or $C_{1-6}$alkoxycarbonyl, $RCF_2O$, an ethoxy group substituted by 3 to 5 fluorine atoms; R$^2$ and R$^3$ together form a group —O(CR$_2$)$_m$O— where m is 1 or 2, and each group R is hydrogen or fluorine;

n is 0 or 1;

R$^5$ and R$^6$ are the same or different and are each hydrogen, $C_{1-6}$alkyl or $C_{3-6}$cycloalkyl, or R$^5$ and R$^6$ together with the nitrogen atom to which they are attached form an azetidino, pyrrolidino, piperidino, piperazino, N-$C_{1-4}$alkylpiperazino or morpholino group; and one of X and Y is a nitrogen atom, and the other is a group CR$^7$ where R$^7$ is hydrogen, $C_{1-4}$alkyl or $NH_2$, or a pharmaceutically acceptable salt thereof.

2. A compound as claimed in claim 1 in which n is 1.

3. A compound as claimed in claim 1 in which R$^5$ and R$^6$ together with the nitrogen claim to which they are attached form a pyrrolidino, piperidino, piperazino, N$C_{1-4}$alkyl piperazino, or morpholino group.

4. A pharmaceutical composition comprising a compound as claimed in claim 1 in association with a pharmaceutically acceptable carrier.

5. A pharmaceutical composition comprising a compound as claimed in claim 2, in association with a pharmaceutically acceptable carrier.

6. A pharmaceutical composition as claimed in claim 5, in a form suitable for oral administration.

7. A pharmaceutical composition as claimed in claim 6, provided with an enteric coating.

8. A pharmaceutical composition as claimed in claim 4 in a form suitable for intravenous administration.

9. A method of inhibiting gastric acid secretion which comprises administering to a mammal in need thereof an effective amount of a compound as claimed in claim 1.

10. A method of treatment of gastrointerstinal diseases and other conditions caused or exacerbated by gastric acidity which comprises administering to a mammal in need thereof an effective amount of a compound as claimed in claim 1.

* * * * *